United States Patent [19]

de Lasa et al.

[11] Patent Number: 4,659,218

[45] Date of Patent: Apr. 21, 1987

[54] MULTI-PROBE SYSTEM FOR MEASURING BUBBLE CHARACTERISTICS GAS HOLD-UP, LIQUID HOLD-UP AND SOLID HOLD-UP IN A THREE-PHASE FLUIDIZED BED

[75] Inventors: Hugo I. de Lasa; Shiun-Liang Lee; Maurice A. Bergougnou, all of London, Canada

[73] Assignee: Canadian Patents & Development Corporation, Canada

[21] Appl. No.: 737,059

[22] Filed: May 23, 1985

[51] Int. Cl.$^4$ ............................................. G01N 21/41
[52] U.S. Cl. .................................. 356/133; 73/861.04; 250/227; 250/574; 356/28; 356/335
[58] Field of Search .................. 356/73, 28, 28.5, 335, 356/133; 250/573, 574, 227; 73/861, 861.04

[56] References Cited

U.S. PATENT DOCUMENTS 4,240,747 12/1980 Harmer ............................... 356/133
4,516,432 5/1985 Hironaga et al. .................... 250/574

OTHER PUBLICATIONS

Miller et al., *Journal British Nuclear Energy Society*, vol. 9, No. 2, Apr. 1970, pp. 94–100.
Abuaf et al., *Review of Scientific Instruments*, vol. 49, No. 8, Aug. 1978, pp. 1090–1094.
Ishida et al., *Powder Technology*, vol. 27, No. 1, Sep.-Oct. 1980, pp. 1–6.
Vasalos, I. A., et al., "Hold-Up Correlations in Slurry Fluidized Beds" AIChE Journal, vol. 28, 346 (1982).
Proceedings—vol. 2 of the 33rd Canadian Chemical Engineering Conference of Oct. 2, 1983, pp. 503–507.

*Primary Examiner*—F. L. Evans

*Attorney, Agent, or Firm*—Finnegan, Henderson, Farabow, Garrett & Dunner

[57] ABSTRACT

Method and apparatus are disclosed for determining one or more physical characteristics of individual bubbles in a gas-liquid system and a gas-liquid-solid system at high temperatures and pressures. An in situ probe device is inserted into the system over which individual bubbles flow. The probe device has a plurality of independent probes. Each has a rounded fibre optic end portion projecting into the system. A source of incident light is directed onto each of the probes. The rounded end portion of each probe is formed with a radius of curvature sufficiently large whereby the angle of incidence of the source light at the rounded portion is greater than the angle of total reflection for the fibre optic when in contact with the gas. The angle of incidence is less than the angle of total reflection for the fibre optic when in contact with the liquid. The plurality of probes are spatially arranged to detect one or more of the bubble physical characteristics as a bubble flows over the probe device. The change in light intensity of reflected light emerging from the probe is measured. The change in light intensities of each of the probes over time is evaluated to determine the one or more bubble characteristics. Each probe is formed of sufficiently thin fibre optic and spaced from the other probes of the device to enable detection of the bubble characteristics for individual bubbles flowing over the probe device. This probe system enables the monitoring of physical characteristics of bubbles in two and three phase systems in an efficient, reliable, economical manner. The system also provides for a measure of solid, gas and liquid hold-ups in a three-phase system.

26 Claims, 19 Drawing Figures

CORRELATION BETWEEN THE SOLID VOLUMETRIC
CONCENTRATION AND THE BASELINE LEVEL

MULTI-PROBE SYSTEM FOR MEASURING BUBBLE CHARACTERISTICS GAS HOLD-UP, LIQUID HOLD-UP AND SOLID HOLD-UP IN A THREE-PHASE FLUIDIZED BED

FIELD OF THE INVENTION

This invention relates to probes for determining one or more physical characteristics of individual bubbles in a gas-liquid phase system or a gas-liquid-solid particulate phase system.

BACKGROUND OF THE INVENTION

Two- and three-phase systems are often employed in chemical reactions. In systems involving the use of reactant gas, the gas is normally contacted with the liquid or solid by bubbling it through the two or three phase system. In these systems, particularly with gas-liquid and gas-liquid-solid particulate phases, the bubble velocity and bubble size become very important parameters in determining behavior of the system and its performance. Such characteristics are particularly important with three phase fluidized beds where the gas and liquid phases act as a media for fluidizing the solid phase. The physical characteristics of the bubbles in fluidized beds affect segregation between reacting phases, bed mixing, particle entrainment from a dense bed, gas hold-up and solid hold-up, mass transfer between the gas and the liquid phase and the solid particulate phase, heat transfer to immersed tube exchangers and bed expansion. Particulate catalysts are used in petro-chemical hydrocracking processes and with newly developed very active catalysts, conversion is limited by the transfer of hydrogen from the bubbles in the three phase system to the liquid phase.

Presently, unsatisfactory devices are available for measuring bubble characteristics in three phase fluidized bed systems. In situ sensors have been used; however, they require special design to minimize flow disturbances. Systems, which require bubble sensors, tend to operate at high temperatures and pressures; for example, conditions of heavy oil hydrocracking processes Fischer-Tropsch reactors and H-coal units. Presently, there are no commercially available bubble sensors or probes which can be used in the extreme environments of heavy oil hydrocracking or coal liquefaction reactor.

In the process industry, bar level detectors are in use to control the liquid level in liquid containers. The bar level detector is made of a glass bar having an end with a prismatic shape close to 45° angle which, when it contacts water, beam refraction takes place. When the end is in water, no or low light levels are recorded due to refraction and consequent loss of light energy into the liquid. A photodetector may be used to detect the intensity of light reflected back out of the bar probe. When the bar probe is in the air of the tank, total reflection of the beam takes place and in that instance, a significant increase in light intensity impinging on the photodetector is observed. The changes of light intensity transformed into voltage variations in the photodetector provide the information for an accurate control of liquid tank levels.

Many other types of optical probes are known for use in measuring changes in composition of two and three phase systems. Optical fibre probes have been used in a variety of configurations to detect changes in various parameters of compositions of two and three phase systems. An example is disclosed in U.S. Pat. No. 4,240,747. A fibre optic probe of a diameter of approximately 1.75 millimeters is formed into various complex curved shapes. The formed probe is placed in a liquid. Light emerging from the probe is sensed to provide information which represents the refractive index of a liquid. The probe may be also used to detect the presence of gas bubbles in a liquid where a high frequency fluctuation in the signal at the output section of the probe indicates the presence of the gas bubbles. The high frequency variation of the output signal is due to the probe being considerably larger than the individual bubbles in the system, so that many bubbles pass at one time over the probe causing a rapid variation in the output signal of light reflected in the probe.

One of the difficulties with three-phase fluidized bed systems is to provide a system which can properly assess local solid hold-ups in the fluidized bed. Electro-conductivity probes have been used which respond to the difference between liquid, solids and gas dielectric constants and conductivities. However, this approach is limited to systems where the appropriate combination of electrical properties allows the evaluation of the various hold-ups. The system is not readily applicable to catalytic hydrocracking of hydrocarbons or coal liquefaction, because the liquid phase has a very low electro-conductivity.

Gamma absorption techniques have been used to assess local hold-ups of solids in fluidized bed systems. The probes used in the gamma absorption technique cannot be arranged in a multi-probe configuration with probes spaced one to two centimeters apart without interference, resulting in the gas liquid and solid hold-ups not being measured simultaneously. This system is disclosed in Vasalos, I. A., D. N. Rundell, K. E. Megiris and G. J. Tjatjopoulos, "Hold-Up Correlations in Slurry Solid Fluidized Beds", *AIChE Journal*, 28, 2, 346 (1982).

The problem with existing techniques in determining local hold-ups in fluidized beds is that only average hold-up values are provided. In an only very limited situations can local hold-ups be determined by electro-conductivity probes.

A multi-probe system disclosed in the Proceedings-Volume 2 of the 33rd Canadian Chemical Engineering Conference of Oct. 2, 1983 uses optical fibre probes for measuring characteristics of bubbles in a three phase fluidized bed system. The probes are each of a U-shape; however, their geometry is not provided. The multi-probe system is capable of measuring bubble velocity and bubble cord length by use of four probes at a vertical separation of 1.25 centimeters. A helium neon laser is used as a source of incident light. Perturbations of light transmitted through the individual probes is detected by a photodetector each time a bubble contacts the respective probe. An analog signal from the photodetector is converted into digital information to provide a basis for analysis of the bubble physical characteristics. This use of the multi-probe system to measure bubble physical characteristics does not contemplate the manner in which the multi-probe system may be used in evaluating, simultanesouly, local gas, liquid and solid hold-ups in a fluidized bed system.

SUMMARY OF THE INVENTION

According to an aspect of the invention, a method is provided for determining one or more physical characteristics of individual bubbles in a gas-liquid-solid system. An in situ probe device is inserted into the system over which the individual bubbles flow. The probe device has a plurality of independent probes, each probe having a rounded fibre optic end portion projecting into the system. A source of incident light is directed onto each of the probes of the device.

The rounded end portion is formed with a radius of curvature sufficiently large whereby the angle of incidence of the source light at the rounded portion is greater than the angle of total reflection for the fibre optic when in contact with the gas and the angle of incidence is less than the angle of total reflection for the fibre optic when in contact with the liquid. The plurality of probes are spatially arranged to detect one or more of the bubble physical characteristics as a bubble flows over the probe device. This is accomplished by measuring the change in light intensity of reflected light emerging from each of the probes of the probe device. The change in light intensities emerging from each probe is evaluated over time to determine the one or more bubble characteristics. Each probe is formed of sufficiently thin fibre optic and spaced from the other probes of the device to enable detection of the bubble characteristics for individual bubbles flowing over the probe device.

A base line value is established for measured light intensity emerging from each of the probes of the probe device while the probe is in contact with liquid with normal concentration of particles. A slight change of the base line value in intensity of the reflected light emerging from the probe is detected. The detected slight change in value for light intensity is converted into a value for a concentration of particulate solids in the system adjacent the probe in accordance with a predetermined scheme, which relates particulate solids concentration to a detected increase in light intensity relative to the base line level obtained for the condition of a liquid free of particles.

According to a preferred aspect of the invention, at the same time and because the probes determine the occurrence of bubbles and non-bubbles (liquid-solids) contacting the probes, the gas hold-up can be determined. Once the gas hold-up is known and considering the above, in providing the solid hold-up, then the following equation gives the liquid hold-up:

$$\epsilon_L = 1 - \epsilon_S - \epsilon_G$$

wherein $\epsilon_L$ is the hold-up of the liquid phase, $\epsilon_S$ is the hold-up of the solid phase and $\epsilon_G$ is the hold-up of the gas phase. The fibre optic multi-probe of this invention provides the local hold-ups of the three phases (gas-liquid-solid) involved in a three-phase fludized bed reactor.

According to another aspect of the invention, an apparatus is provided for determining one or more physical characteristics of the individual bubbles in a gas-liquid system. The apparatus comprises an in situ probe device adapted for insertion into the gas liquid system in an area where individual bubbles flow in the system. The probe device comprises a plurality of independent probes. Each of the probes has a rounded fibre optic end portion. Means is provided for directing a source of incident light onto each of the probes. The rounded end portion has a radius of curvature sufficiently large whereby the angle of incidence of the incident light at the rounded portion is greater than the angle of total reflection for the fibre optic when in contact with the gas and the angle of incidence is less than the angle of total reflection for the fibre optic when in contact with the liquid.

The geometric shape of the rounded end portion of the probe is calculated with either of the following formulas:

(a) for the dome-shaped probe, the tip curvature is defined by:

$$\sin \alpha = a/R' \qquad (i)$$

$$\sin \beta = b/R' \qquad (ii)$$

wherein $\alpha$ and $\beta$ are the total reflection angles for gas and liquid respectively, $R'$ is the radius of curvature of the probe, a and b are two characteristic positions in the probe.

(b) for the U-shaped probe, the tip curvature is defined by:

$$\sin \alpha = (R/R+d) \qquad (iii)$$

$$\sin \beta = (R+x/R+d) \qquad (iv)$$

wherein $\alpha$ and $\beta$ are the total reflection angles for gas and liquid respectively, R is the radius of curvature of the U-shaped probe, d is the fibre optic diameter and x is a characteristic position of the fibre cross-section.

The probes of the probe device are spatially arranged relative to each other in a compact fixed manner to permit detection of one or more of such bubble physical characteristics as an individual bubble flows over the probe device. Means detects the change in light intensity of reflected light emerging from each of the probes. Means evaluates the change in light intensity of each probe over time to determine the one or more bubble physical characteristics. The fibre optic of each probe is sufficiently thin to enable detection of the bubble characteristic for individual bubbles flowing over the probe device.

BRIEF DESCRIPTION OF THE DRAWINGS

Preferred embodiments of the invention are shown in the drawings wherein.

DETAILED DESCRIPTION OF THE PREFERRED EMBODIMENTS

Figure 1:
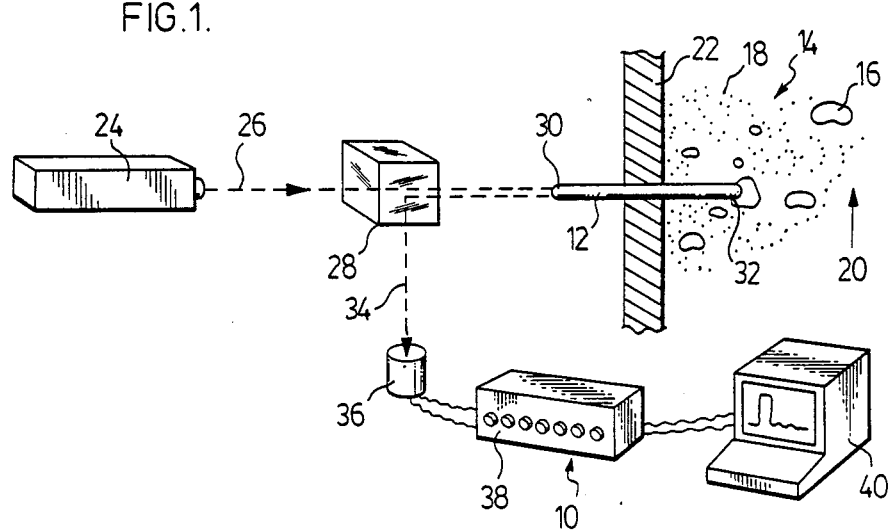
FIG. 1 is a schematic view of the apparatus according to this invention for measuring bubble characteristics.

An apparatus 10 for detecting bubble characteristics in a three phase system is schematically shown in FIG. 1. A probe device includes a plurality of probes 12, only one of which is shown as positioned in situ in the system 14. The plurality of probes 12 may be arranged in a format of FIG. 4. According to this embodiment, the system consists of a liquid medium with gas bubbles 16 and solid particulate matter 18. The bubbles rising in the direction of arrow 20 form a fluidized bed for the system 14 within the reactor wall 22. The probe 12 is secured in the reactor wall to remain fixed at least during the sensing operation. In accordance with this invention, a plurality of probes 12 are provided in association with a probe device, as shown more clearly in FIGS. 3 and 4, to determine various bubble physical characteristics by the apparatus 10. A laser 24 has its source of light as emitted therefrom directed along arrow 26 through a beam splitter 28 onto the exposed end portion 30 of probe 12. The probe 12 functions as a wave guide to permit light to travel to the end of the probe and permit reflected light to travel back out of the probe. Incident light, which is reflected back out of the probe 12 by its rounded tip portion 32, is split off by beam splitter 28 in the direction of arrow 34. A photodetector 36 detects the intensity of reflected emerging light from the probe 12. The photodetector 36 is connected to an analog to digital converter for converting the analog signals from the photodetector 36 into digital signals which are input to the microprocessor 40. Programs are provided in the microprocessor which enable it to evaluate and analyze the input data to determine physical characteristics of the bubbles 16 in the three phase system 14 of the reactor.

Figure 2:
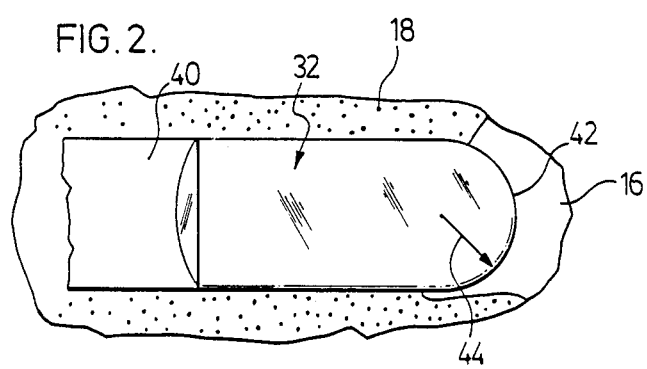
FIG. 2 is a enlarged view of the tip of the probe of FIG. 1.

Various tip configurations may be used for each of the probes 12. An example of a probe tip 32 is shown in FIG. 2. The probe is encased in a sheath portion 40 which may be stainless steel. The stainless steel sheath protects the probe from abrasion along its entire exposed length and also lends structural stability and impact strength to the probe. The exposed tip 32 is a continuation of the fibre optic extending through the sheath 40. According to the preferred embodiment of FIG. 2, the tip end 42 is rounded with a radius of curvature indicated by arrow 44. The radius of curvature 44 for the tip end 42 defines a dome-shaped head which provides the necessary geometric shape for the interface between the medium of the fibre optic and that of the system 14, so that the tip can be utilized to distinguish between solids, liquid and gas bubbles of the system 14.

The basic principle on which the design and shape for the tip end 42 is determined requires a radius of curvature sufficiently large whereby the angle of incidence of the source light at the rounded portion is greater than the angle of total reflection for the fibre optic when in contact with the gas of a bubble and the angle of incidence is less than the angle of total reflection for the fibre optic when in contact with the liquid. With this relationship, a significant fraction of the incident light radiation is reflected at the rounded tip end when the tip is in contact with a gas. However, when the rounded tip end is in contact with a liquid, minimal reflection of the incident light occurs resulting in a significant decrease in reflected radiation emerging from the fibre optic probe.

The shape of the probe tip may be calculated in accordance with the following formulas involving two characteristic angles and which correspond to the angles of total reflection of the probe immersed in air and water respectively:

$$\sin \alpha = a/R' \quad (i)$$

$$\sin \beta = b/R' \quad (ii)$$

wherein $R'$ is the radius of curvature of the probe (44 in FIG. 2), a and b are two characteristic positions in the probe.

For instance if a dome-shaped probe is designed to be used in a through-phase fluidized bed constituted by air-water-particles, a 2 mm fibre optic bar with $R'=1$ mm can be selected.

Figure 2A:
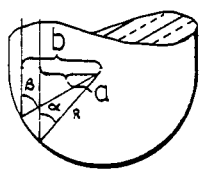
FIGS. 2a and 2b are enlarged views of the probe tip of FIG. 2 showing details of its geometrical shape.
Figure 2B:
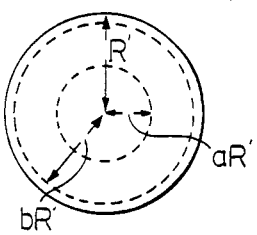

With reference to FIGS. 2(a) and 2(b), the above formulas may be used as follows to calculate probe tip geometrical shape:

(i) for air:
  $\sin \alpha = a/R'$
  $\alpha = 43.3°$ [air-fibre optic(silica cord)]
  $\sin \alpha = \sin 43.3° = 0.6858$
  $R' = 1$ mm
  $a = R' \sin \alpha = 1$ mm $\times 0.6958 = 0.6858$
  $a = 0.6858$ (ii) for water:
  $\sin \beta = b/R'$
  $\beta = 65.8°$ [water-fibre optic(silica cord)]
  $\sin = \sin 65.8° = 0.9121$
  $R' = 1$ mm
  $b = R' \sin \beta = 1$ mm $\times 0.9121 = 0.9121$ mm Based on the above parameters, for air contacting the tip of the probe, $$\text{fraction of the Beam Lost} = \frac{\pi a^2}{\pi R^2} = \frac{0.6858^2}{1^2} = 0.470$$

Therefore, fraction of beam intensity lost when air is contacting the tip is 0.470 and fraction of beam intensity conserved when air is contacting the tip is 0.53.

When water is contacting the tip of the probe.

$$\text{fraction of Beam Lost} = \frac{\pi b^2}{\pi R^2} = \frac{0.9121^2}{1^2} = 0.8319$$

Therefore, the fraction of beam intensity lost when water is contacting the tip is 0.832 and fraction of beam intensity conserved when water is contacting the tip is 0.168.

In an alternative application of the probe device, such as, in heavy oil hydrocracking, the following conditions apply:

| heavy oil | $n = 1.5$ |
|---|---|

-continued

| hydrogen | n = 1 |
| glass bar probe of heavy flint | n = 1.6 |

The following calculation based on the above formulas (i) and (ii) may be made:

sin α=0.625=a/R'
a=0.625×1=0.625 mm
sin β=0.9375=b/R'
b=0.9375×1=0.9375

For H₂ contacting the tip, fraction of beam intensity lost is:

$$\frac{\pi a^2}{\pi R^2} = \frac{0.625^2}{1^2} = 0.390.$$

Therefore, the fraction of beam intensity conserved is 61%.

For heavy oil contacting the tip, fraction of beam intensity lost is:

$$\frac{\pi b^2}{\pi R^2} = \frac{0.9375^2}{1^2} = 0.878$$

Therefore, the fraction of beam intensity conserved is 12.2%.

Figure 3:
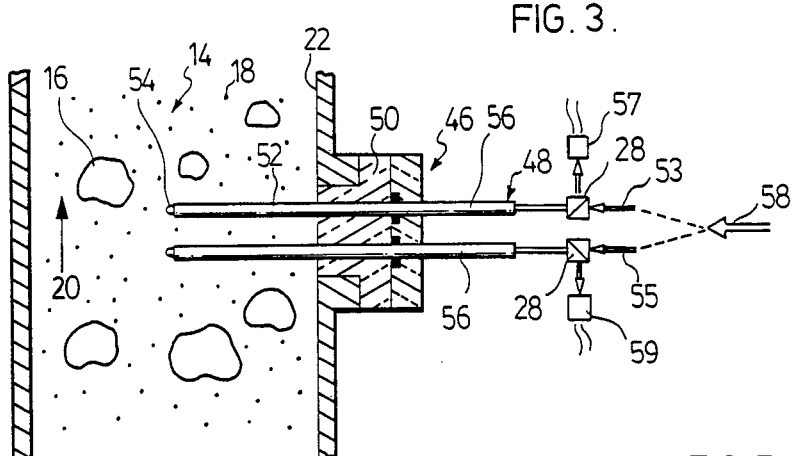
FIG. 3 is a schematic representation of an alternative embodiment for the probe device according to this invention.

FIG. 3 illustrates the dome-shaped probe device 46 mounted in the wall 22 of the fluidized bed reactor. The probe device 46 comprises a plurality of probes 48 which extend through the probe device support portion 50, as mounted in the reactor wall 22. The individual probes 48 have a stainless steel sheath 52 housing the individual probes with the exposed tip end 54. Each probe 48 comprises a wave guide fibre optic 56 which passes through the stainless steel sheath 52 and is shaped at its end in the form of a dome. The incident light from the source travels in the direction of arrow 58 and is split into incident beams 53 and 55. Beam splitters 28 are used to direct the incident beams 53 and 55 into the body portion 56 of each probe of the devices. The reflected light radiation emerges from fibre optic body 56 of each probe and by each beam splitter 28 is directed into photodetectors 57 and 59 at 90° with respect to the fibre optic to detect the intensity of the radiation reflected at the dome-shaped tip 54 of the probe.

Figure 4:
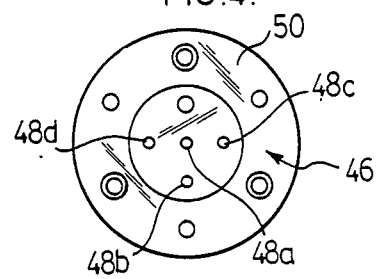
FIG. 4 is a plan front view of the support casing for the individual probes of the probe device.
Figure 5:
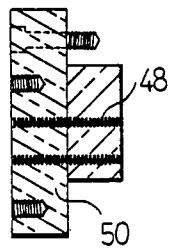
FIG. 5 is a side plan view of the casing for the probe device of FIG. 4.

As shown in FIG. 4, a plurality of the probes 48 are mounted in the support plate 50. The probes, as housed in their stainless steel sheaths, extend through the plate 50 in the manner shown in FIG. 5. According to this preferred embodiment, to detect physical characteristics of the bubbles in terms of bubble velocity, bubble cord height, bubble cap shape and solid hold-ups in the fluidized bed, the probes 48 may be arranged in a T-shaped pattern as shown in FIG. 4. Alternative configurations are useful in this regard which are discussed in FIGS. 13 through 15. Probes 48a and 48b form the first set and probes 48c and 48d form the second set in defining the T-shaped pattern. The first set of probes extend in a direction which is in the same direction as the flow of bubbles over the probe device 46. Probes 48c and 48d extend transversely of this direction and spaced to either side of probe 48a, the purpose of which will be explained with respect to the analysis of the data, shown in FIGS. 7, 8 and 9.

Figure 6:
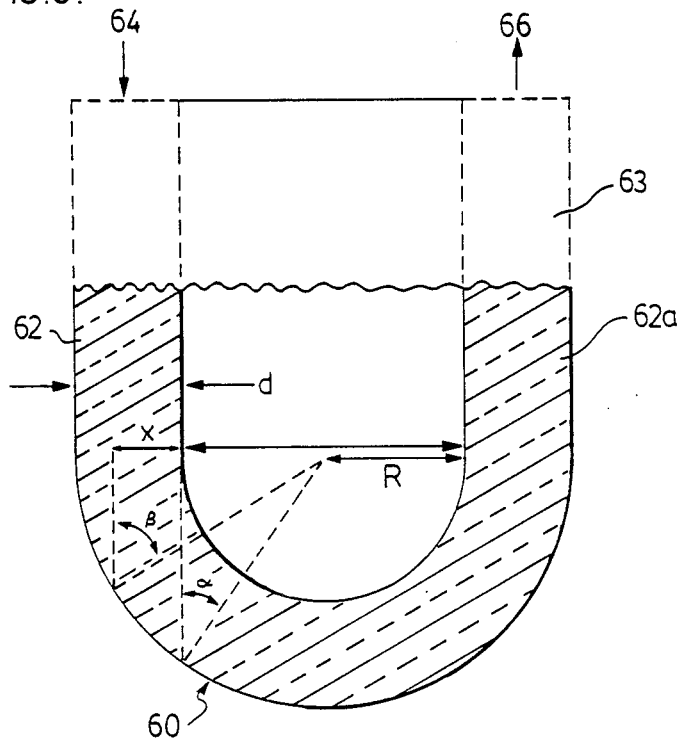
FIG. 6 is an enlarged view of the tip portion of the probe U-shaped.

An alternate shape for the probe tip, as shown in an enlarged scale in FIG. 6, comprises a U-shaped tip 60 with incident arm 62 and return arm 62a of the wave guide. A stainless steel sheath 63 is provided over the tip. The source of light enters the probe in the direction of arrow 64 and reflected, emerges in the direction of arrow 66. In order to meet the above qualifications regarding the shape of the fibre optic probe tip 60, the characteristic angle of the U-shaped probe, which is the total reflection angle for the probe in water, and the characteristic angle of the U-shaped probe which is the total reflection angle for air are defined in accordance with the following formulas:

$$\sin \alpha = (R/R+d) \qquad (iii)$$

$$\sin \beta = (R+x/R+d) \qquad (iv)$$

wherein R is the radius of curvature of the U-shaped probe, d is the fibre optic diameter and x is a characteristic position of the fibre cross-section as shown in FIG. 6. As an example, in the situation where α and β are selected for air and water respectively, then α equals 43.3° for air and β equals 65.8° for water. Assuming a fibre optic diameter of 0.4 mm, R is then equal to 0.87 mm and x is equal to 0.29 mm. These values indicate that all light rays positioned on the right side of x=0.29 mm position as shown in FIG. 6 will be lost after the first reflection. The light rays on the left side of the x position will be kept inside the fibre after the first reflection. Comparing x with d, a ratio of 0.725=x/d is obtained and one could expect that when the probe is immersed in water, after the first reflection, 77.6% of the beam will be refracted and dispersed, while 22.4% will be conserved in the fibre. The special condition of the probe design is that a total reflection for the gas phase occurs without partial refraction for the liquid phase to provide the necessary perturbations at the emergent side 66 of the probe.

It is appreciated that the principle of "total reflection-partial refraction" for a U-shaped probe and "partial reflection and partial refraction" for a dome-shaped probe can be achieved as well in a system constituted by heavy oil and hydrogen with 1.5 and 1.0 refraction indices respectively. This type of system, using particulate catalysts, is common to heavy oil hydrocracking reactors where the probe device, according to this invention, can be used. With heavy oil systems, the material of the probe is selected so as to provide a refraction index of 1.6. Acceptable materials, which have a refraction index in excess of 1.6 for the wavelengths of the light energy to be used, are various grades of flint glass. Under these conditions, in accordance with the above formulas, the incident light will be conserved when the U-shaped probe is contacted with hydrogen and only 17% of the intensity of the beam will be transmitted to the emerging arm 66 when the probe is contacted by heavy oil. For the dome-shaped fibre, then 61% of the beam will be conserved when exposed to hydrogen and only 12.2% when contacted with heavy oil. It is appreciated that the dome-shaped probe of FIG. 2, being of a solid rod as compared to the U-shaped probe of FIG. 6, has greater mechanical strength compared to the U-shaped probe. Therefore, environments where the probes are subjected to physical abuse, such as mechanical shock abrasion and the like, the dome-shaped probe is preferred. Such conditions occur in heavy oil hydrocrackers so that in those systems, the use of the dome-shaped probe is normal.

Figure 7:
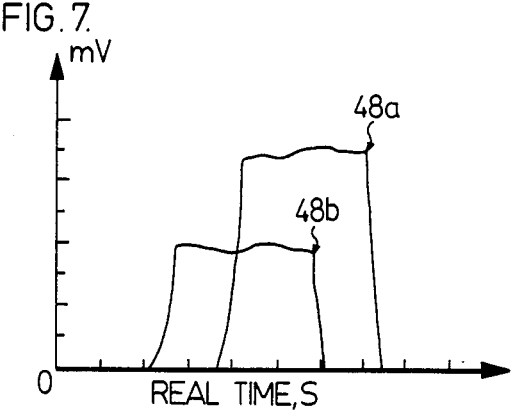
FIG. 7 is a graph showing the photodetector output in millivolts versus time for the two vertical probes of FIG. 4 when a bubble flows over the probe device.
Figure 8:
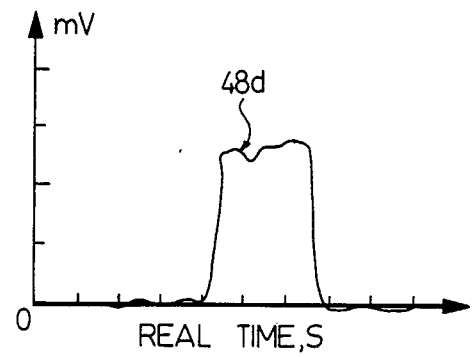
FIGS. 8 and 9 are graphs showing the output of the photodetector in millivolts versus time for a bubble flowing over the outer probes of FIG. 4.
Figure 9:
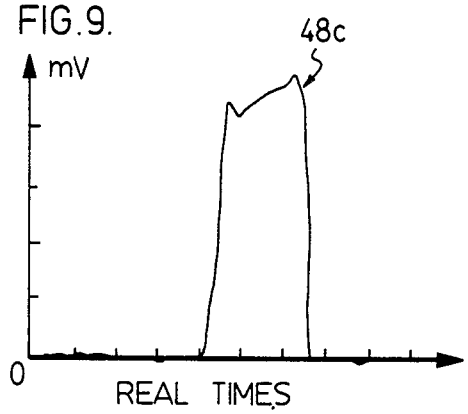

From the spatial relationship and known predetermined spacing between the probes, as shown in FIG. 4, physical characteristics of the bubbles may be determined such as bubble velocity, bubble cord length and bubble included angle, that is the shape of the bubble cap. Typical generally square waves were recorded when a gas bubble contacts the probe device and flows over it is shown in FIGS. 7, 8 and 9. In FIG. 7, where the bubble flows upwardly over the probe device 46, the square wave for probe 48b is shown. The bubble is obviously of a cord length greater than the distance between the probes 48a and 48b, because the square wave produced by the bubble flowing over the probe 48a overlaps in real time the square wave for probe 48b. From the values of FIG. 7, the bubble velocity and bubble cord length may be calculated. Upon locating on the graph the starting and ending points of these square waves for probes 48a and 48b, the mean value estimated with the first statistical moment is applied to the data and the duration of each signal may be calculated. The duration of time for each gradation in FIGS. 7, 8 and 9 is approximately 0.008 seconds. Normally, only signals coming from probes 48a and 48b are used in calculating velocity and probe cord length, where such signals fit the requirement of a standard deviation of the square waves smaller than 10%. With this constraint on the data used, virtually all the bubbles selected for analysis of their physical characteristics travel in a relatively straight upward manner. The bubble velocity is calculated knowing the distance between the probes 48a and 48b and dividing it by the separation in the mean values for the real times of the square waves representative of the flow of the bubble over the probe device. The cord length of the bubble may then be calculated by the product of bubble velocity and the duration of the square wave signal which indicates the length of time it takes for an individual bubble to flow over a probe of the probe device 46.

Figure 10:
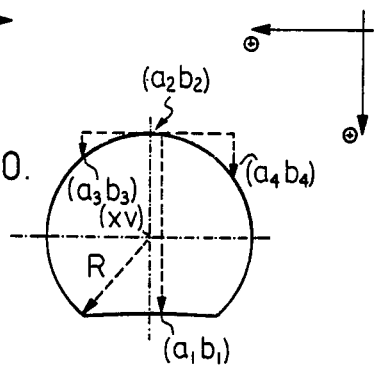
FIG. 10 is a representative sketch of a bubble illustrating its cap portion and the parameters for calculating the cap shape.

Another aspect of the multi-probe device, that can be either consituted by dome-shaped probes or U-shaped probes, is to determine the shape of the bubble cap, as shown in FIG. 10 and to assist in providing a careful screen of the experimental data obtained from the first set of probes. The shape and size of the bubble may be reconstructed using the top three probes and comparing the changes in the signals of the top three probes 48a, 48c and 48d. From this information, the central bubble cord may be estimated based on the formulas:

$$L = R - (y - b_1)$$

wherein L is axial bubble length, R is radius curvature of the spherical bubble cap; y is the characteristic ordinant giving the distance between the central probe and the centre of the circumference containing the spherical cap and $b_1$ is the ordinant of point 1 of FIG. 10. R may be calculated in accordance with the formula:

$$R = (x^2 + y^2)0.5,$$

wherein x is the characteristic abscissa giving the distance between the centre of the circumference containing the spherical cap and y is as defined above. The characteristic dimensions of this spherical cap may then be calculated in accordance with the formulas:

$$x = [(a_4^2 + b_4^2)b_3 - (b_3^2 + a_3^2)b_4]/[2(a_4 b_3 - a_3 b_4)]$$

$$y = (a_3^2 + b_3^2 - 2a_3 x)/2b_3$$

wherein $a_1$ is the abscissa of point 1 of FIG. 10; $a_2$ is the abscissa of point 2 of FIG. 10; $a_3$ is the abscissa point 3 of FIG. 10 and $a_4$ is the abscissa of point 4 of FIG. 10. Similarly, $b_1$ through $b_4$ are the ordinants of the respective points 1 through 4 of FIG. 10. The square wave signals of FIGS. 8 and 9 thereby provide the necessary information in calculating the shape of the physical bubble cap, in accordance with the above formulas.

The multi-probe device is also useful in assessing particle hold-up in two-phase fluidized bed (liquid solid) or three phase fluidized beds (gas-liquid-solid) involving a liquid and a particulate solid, such as a catalyst. This system is useful in catalytic heavy oil hydrocracking, coal liquefaction reactors and Fischer-Tropsch fludized units to assess catalyst hold-up at various levels in the fluidized bed reactor. By use of the fibre optic probes that withstand the high pressure and temperatures of these reactors, according to this invention, the incident light interacts with the rounded surface where the reflected beam is physically displaced from its point of incidence with the surface. This effect is a result of a reflected beam crossing the interface between the probe and the surrounding liquid, propagating through the liquid, interacting with adjacent virtual surfaces and re-entering into the fibre optic slightly displaced. This shift in the incident beam is referred to as the Goos-Haenchen effect. With this shift in the incident beam, the intensity of the emerging reflected light will vary slightly from a base line value representative of the liquid medium free of particles compared to when particulate catalyst is adjacent the probe surface. Therefore, over time in operation of the system, a base line value for the intensity of the emerging light can be established. Any slight increase to a new level in reflected light intensity from the base line can be interpreted as being caused by a change in the fraction of particulate matter remaining adjacent the probe surface, thereby indicating a new hold-up of solid particulate matter in that area of the fluidized bed reactor.

Figure 12:
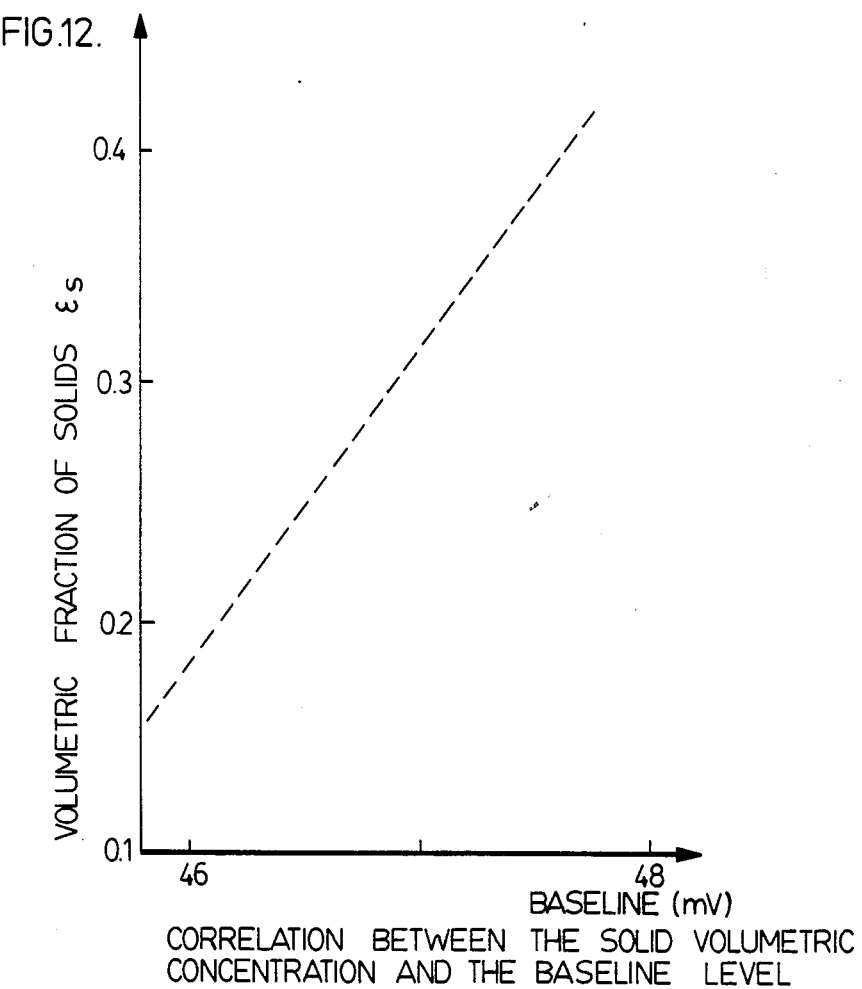
FIG. 12 is a plot of volumetric fraction of solids in the system versus photodetector output in millivolts.

Referring to FIG. 12, a plot of the volumetric fraction of solids versus the base line signal from the photodetector in millivolts indicates a linear relationship between an increase in solids adjacent the probe with corresponding increase in the output signal of the photodetector. As is apparent from FIGS. 7 through 9, there is a considerable change in the photodetector signal when a gas bubble contacts and flows over one or more of the probes of the probe device. By establishing a base line value for the output of the photodetector, when the probe device is immersed in the liquid and a normal concentration of solids is in liquid about the probe device, then the solid particle concentration in that region of the reactor can be measured. A slight change in the base line value indicates particulate hold-up changes in that area of the unit. Conversely, a constant base line value for the output signal of the photodetector indicates that no significant particulate catalyst hold-up variation takes place in that region of the fluidized bed reactor. As per FIG. 12, the relationship of volumetric fraction of solids to various base line output voltages of the photodetector is provided. The approximately linear relationship between the volumetric fraction of solids and the base line level may be used develop a mathematical scheme or algorithm which can be used to calculate the solid hold-up in the reactor system due to the detected slight change in output of the photodetector, which may vary from no output up to 2 millivolts.

According to another aspect of the invention, aside from using the probe device to determine hold-up of particulate catalysts in the region of the probe, hold-up values for the liquid and gas can also be determined. The probe device, from which the various outputs are obtained and analyzed, allows one to determine the occurrence of bubbles and non-bubbles contacting the probes. From this information, the gas hold-up can be determined in providing values for solid hold-up and gas hold-up. The equation, which provides the relationship of solid hold-up, gas hold-up and liquid hold-up, is as follows:

$$\epsilon_L = 1 - \epsilon_S - \epsilon_G$$

wherein $\epsilon_L$ is the hold-up of the liquid phase, $\epsilon_S$ is the hold-up of the solid phase and $\epsilon_G$ is the hold-up of the gas phase. Substituting the calculated values for $\epsilon_S$ and $\epsilon_G$ in the above equation, a value for $\epsilon_L$ can be obtained. Therefore, according to this invention by use of the probe device, values of the hold-ups of all phases in the reactor can be calculated to optimize in the reaction efficiencies of the reactor. This system will be discussed in more detail with respect to FIG. 16.

Figure 11:
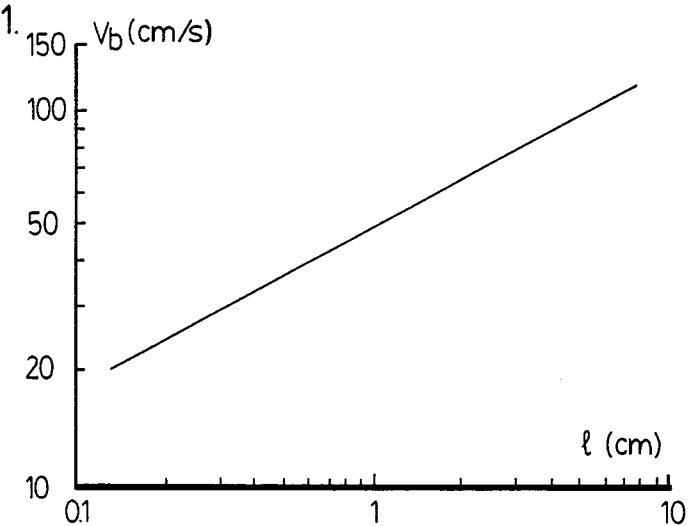
FIG. 11 is a plot of bubble velocity versus the cord length of the corresponding bubble.

The multi-probe device, according to this invention, with the plurality of dome-shaped or U-shaped fibre optic tip portions is capable of measuring several bubble physical characteristics which, when known, can result in a more effective operation for a gas-liquid or gas-liquid-solid contacting system. For example, in three phase fluidized bed systems, bubble velocity, bubble cap shape, bubble cord length and gas liquid solid hold-ups provide very useful information in the control and optimized operation of the fluidized bed reactor. A further aspect which is considered in the operation of the fluidized bed reactors is the relationship of the bubble velocity to the bubble cord length. As shown in FIG. 11, there is a correlation between the bubble velocity and the cord length which may be expressed by the formula:

$$V_b = qL^z$$

wherein q and z are coefficients of the bubble velocity correlation, "L" is the axial bubble cord length and $V_b$ is the relative velocity of the bubble with respect to the liquid. For various values of $V_1$, which is the superficial liquid velocity in centimeters per second, it is apparent from FIG. 11 that the correlation of bubble velocity to cord length exists and can be predicted in accordance with the above formula. For the particular parameters prescribed in FIG. 11, q has the value of 47.08±1.04 and z has the value of 0.4302±0.05 in the bubble velocity correlation. The following Table I sets out results obtained for various values of $V_1$.

TABLE I

| | Bubble Velocity Correlation q and z Parameters ($V_g$ = 1.214 cm/s) | | | |
|---|---|---|---|---|
| Run | Number of Bubbles | $V_1$ cm/s | q | z |
| 1 | 7 | 0.389 | 39.77 | 0.2784 |
| 2 | 28 | 0.778 | 43.75 | 0.5279 |
| 3 | 23 | 1.167 | 47.06 | 0.413 |
| 4 | 19 | 1.556 | 49.03 | 0.4188 |
| 5 | 34 | 1.945 | 50.61 | 0.4507 |

TABLE I-continued

| | Bubble Velocity Correlation q and z Parameters ($V_g$ = 1.214 cm/s) | | | |
|---|---|---|---|---|
| Run | Number of Bubbles | $V_1$ cm/s | q | z |
| 1 + 2 + 3 + 4 + 5 | 111 | — | 47.08 | 0.4302 |

As shown in Table I, the values for q and z are consistent for various values of $V_1$ to provide thereby a correlation between the bubble cord length and the bubble velocity to assist in predicting and controlling fluidized bed reactors.

It is appreciated that the manner in which the data from the probe is analyzed can be accomplished in a variety of ways. Following the procedures set out with respect to the system shown in the drawings and using a computer facility to make the necessary calculations, according to the embodiment of FIG. 1, a high speed analog to digital converter, which is operated at 2500 samples per second (maximum capacity: 50000 samples/second), is used for digitizing and providing an input to the microprocessor 40. A variety of microprocessors may be used such as that sold by Hewlett Packard under model numbers HP9826 and HP1000 for analyzing the input data in accordance with the above formulas to ascertain the various desired physical characteristics of the bubbles. By way of programing the microprocessor, the calculations based on the input data corresponding measured information from the probes of the multi-probe device can be made to provide the information on the desired physical characteristics of the bubbles.

By use of U-shaped probes having fibre optic of approximately 400 μm diameter with the radius of curvature of approximately 0.5 mm, or dome-shaped probes made out of 2 mm diameter fibres with a 1 mm radius of curvature at the probe tip, the probes may be located to measure conveniently various bubble sizes. The four probe devices of the first set used in a column, FIG. 4, may be spaced apart 1.25 cm.

Figure 13:
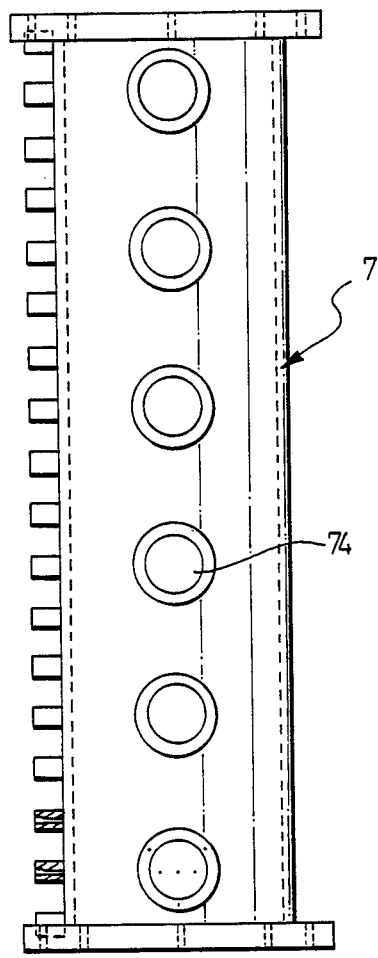
FIG. 13 is a side elevation of a cylindrical fluidized reactor bed.
Figure 14:
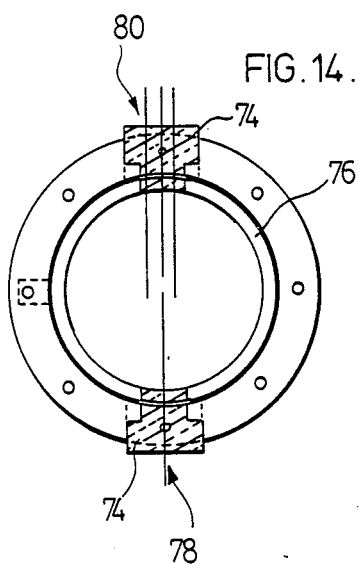
FIG. 14 is a section through the reactor of FIG. 13.
Figures 15A, 15B:
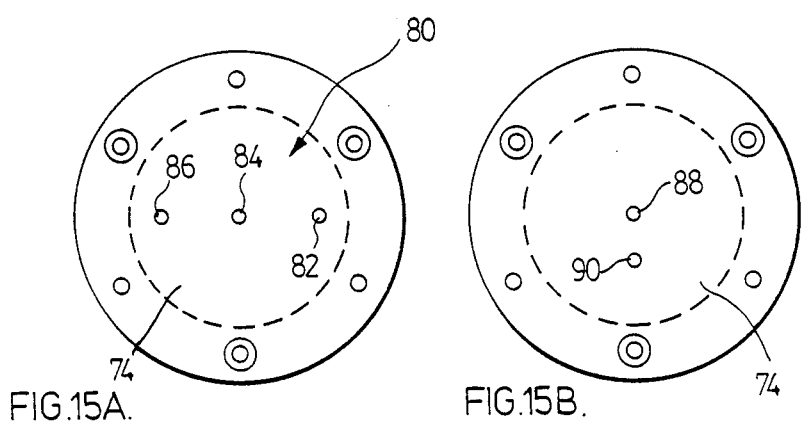
FIGS. 15a and 15b are plane views of the probe device on each side of the reactor as shown in the section of FIG. 14.

An alternative configuration for the probes and their numbers is shown in FIGS. 13 through 15. A cylindrical reactor column 72, as shown in FIG. 13, consists of a plurality of probe support devices 74 located various vertical levels along the height of the reactor 72. The probe support devices are mounted in the wall portion 76 of the reactor in the manner shown in FIG. 14. Separate probe support devices 74 are mounted in each side of the reactor where probe device 78 consists of two probes oriented in the vertical direction. Probe device 80 consists of three individual probes oriented in the horizontal direction. With reference to FIGS. 15(a) and 15(b), the probe device 80 shows the horizontal orientation for the separate probes 82, 84 and 86. Similarly, FIG. 15(b) shows the vertical orientation for the two probes 88 and 90. This arrangement, therefore, provides five probes in the system where the vertical probes are located in the column opposite the horizontal set of probes to provide for an alternative form in measuring the characteristics of the bubbles and solid and liquid gas hold-ups. The two probes 88 and 90 of probe device 78 are located with a vertical separation of 0.95 cm. The remaining three probes 82, 84 and 86 of probe device 80 are positioned at the same level as probe 88. Probes 82 and 86 are spaced to each side of probe 84 0.95 cm. The outer probes 82 and 86 extend inwardly further than the central probe 84 to provide for a 120° circumferential separation between the central probe 88 distal end and the distal ends 82 and 86 of the outer probes.

This arrangement for the probe devices entering the reactor column from each side are capable of measuring axial bubble cord lenght as short as in the range of 0.2 cm.

Figure 16:
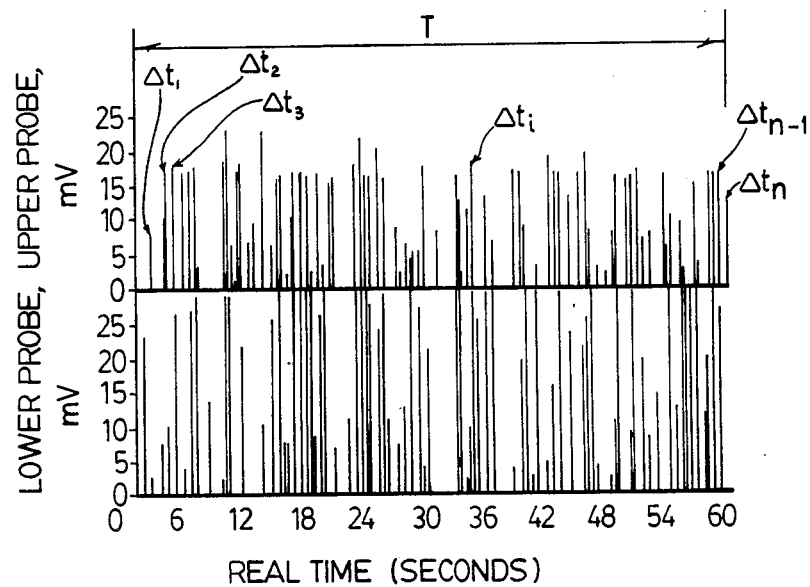
FIG. 16 is a plot of photodetector output for upper and lower probes of the device of FIG. 15 versus time.

With reference to FIG. 16, the $\epsilon_G$, the hold-up of the gas phase may be calculated. Photodetectors are provided in association with probes 88 and 90 of FIG. 15b. A sudden increase in each photodetector output indicates a bubble having passed over the probe where each spike in FIG. 16 is representative of each square wave of, for example, the enlarged plot of FIG. 7. Each bubble passes over the probe tip during a finite time which is in terms of a small fraction of a second such as in the range of 25 milliseconds to 30 milliseconds. The duration for each bubble to pass over the probe tip may be represented by $\Delta t$. The gas hold-up in the system can be calculated in accordance with the formula:

$$\epsilon_G = \frac{\sum_{1}^{n} \Delta t_i}{T}$$

wherein $\epsilon_G$ is the hold-up of the gas phase;

$\Delta t_i$ is the duration for the ith bubble to pass over the probe tip; and

T is the period during which all of the bubbles 1 through n were detected by the upper probe.

Knowing the value for $\epsilon_S$ calculated in the manner previously described, and calculating $\epsilon_G$ as per the above, then the hold-up of the liquid phase $\epsilon_L$ is calculated as per the formula:

$$\epsilon_L = 1 - \epsilon_S - \epsilon_G$$

From FIG. 16, it is also possible to calculate bubble frequency; i.e., how may bubbles per second contact the probe tip. For the lower probe, the bubble frequency is 2.23 bubbles per second whereas the bubble frequency for the upper probe is 2.30 bubbles per second which provides an average bubble frequency of 2.27 bubbles per second.

Although preferred embodiments of the invention have been described herein in detail, it will be understood by those skilled in the art that variations may be made thereto without departing from the spirit of the invention or the scope of the appended claims.

We claim:

1. A method for determining one or more physical characteristics of individual bubbles and particle solid hold-up in a gas-liquid-particulate solid system by use of an in situ probe device inserted into said system over which said individual bubbles and solid particle flow, said probe device having a plurality of independent probes, each having a rounded fibre optic end portion projecting into said system, directing a source of incident light onto each of said probes of said device, said rounded end portion being formed with a radius of curvature sufficiently large whereby the angle of incidence of said source light at said rounded portion is greater than the angle of total reflection for said fibre optic when in contact with said gas and the angle of incidence is less than the angle of total reflection for said fibre optic when in contact with said liquid, spatially arranging said plurality of probes of said probe device to detect one or more of said bubble physical characteristics as a bubble flows over said probe device, measuring the change in light intensity of reflected light emerging from each said probe, evaluating said change in light intensities of each said probe over time to determine said one or more bubble characteristics, each said probe being formed of sufficiently thin fibre optic and spaced from said other probes of said device to enable detection of said bubble characteristics for individual bubbles flowing over said probe device, establishing a base line value for measured light intensity emerging from each said probe while said probe is in contact with said liquid and particles, detecting a slight increase relative to said base line value in intensity of said reflected light emerging from said probe, converting said detected slight increase into a value for increased concentration of said particulate solids in said system adjacent said probe in accordance with a predetermined scheme which relates particulate solids concentration to a detected increase in said light intensity relative to said base line value of light intensity of said emerging light.

2. A method of claim 1, wherein said probe device is adapted by way of a particular spatial arrangement of said probes to determine bubble velocity and cord length of an individual bubble as it flows over said probe device.

3. A method of claim 2, wherein said gas liquid system is fluidized with said bubbles.

4. A method of claim 1 further characterized in determining one or more bubble characteristics in a three phase gas-liquid-solid particulate system which is fluidized by said bubbles.

5. A method of claim 4 adapted to determine said bubble physical characteristics in a petroleum hydrocracking system, a coal liquefaction reactor and a Fischer-Tropsch reactor.

6. A method of claim 5, wherein each of said probes is formed of a material having an index of refraction greater than 1.55 for a particular wavelength of said source of light.

7. A method of claim 5, wherein each of said probes is formed of a flint glass.

8. A method of claim 1, wherein each said probe is a fibre optic rod having a rounded tip which is located in said system, said rounded tip for said fibre optic rod being determined in accordance with the formulas:

$$\sin \alpha = a/R' \qquad \text{(i)}$$

and $$\sin \beta = b/R' \qquad \text{(ii)}$$

wherein $\alpha$ and $\beta$ are the total reflection angles for gas and liquid respectively, R' is the radius of curvature of the tip of the probe, a and b are two characteristic positions in the probe.

9. A method of claim 1, wherein each said probe is circular in cross-section fibre optic material which is formed into a U-shaped tip, locating said tip in said system, the shape of said tip being determined in accordance with the formulas:

$$\sin \alpha = (R/R+d) \qquad \text{(iii)}$$

$$\sin \beta = (R+x/R+d) \qquad \text{(iv)}$$

wherein R is the radius of curvature of said U-shape tip, d is the fibre optic diameter, x is a characteristic position of the fibre cross-section, α is the total reflection angle for said gas and β is the total reflection angle for said liquid.

10. A method of claim 1, wherein said probes of said device are spatially arranged to provide a first set of at least two probes spaced apart a predetermined distance and extending in the direction of flow of said bubbles over said probe device; a second set of at least two additional probes spaced apart a predetermined distance and arranged to extend transversely of said direction in which said first set of probes extend, arranging said probes of said first and second sets to be spaced apart in a sufficiently compact manner to enable a determination of said physical characteristics, determining individual bubble velocity by measuring a first period of time that said individual bubble takes in flowing over said predetermined distance and calculating bubble velocity determining cord length of said individual bubble by measuring a second period of time, that said individual bubble takes in flowing over one of said probes and calculating axial cord length from the product of said calculated velocity and said measured second period of time, determining bubble cap shape by comparing relative times when said emerging light intensity significantly changes and calculating bubble cap shape from said comparison based on a predetermined spatial arrangement for said second set of probes.

11. A method of claim 1, further characterized in directing a source of light from a laser of predetermined wavelength onto each of said probes and measuring intensity of said reflected light emerging from said corresponding probe with a photodetector.

12. A method of claim 11, wherein said laser is a Ne/He laser emitting monochromatic light with a wavelength of 0.632 microns.

13. A method of claim 12, wherein said proves are formed of flint glass optic fibre, the fibre having a diameter of approximately 1 to 3 mm.

14. A method of claim 1 further comprising determining the duration of change in light intensity emerging from said probe due to a bubble passing over said probe tip, making several of said determinations of duration for bubble passage over said probe tip, converting said several determinations made during a measured period of time into a value for hold-up of the gas phase $\epsilon_G$ in accordance with the formula:

$$\epsilon_G = \frac{\sum\limits_{1}^{n} \Delta t_i}{T}$$

wherein
$\epsilon_G$ is the hold-up of the gas phase;
$\Delta t_i$ is the duration for the ith bubble to pass over the probe tip; and
T is the period during which all of the bubbles 1 through n were detected by the upper probe.

15. A method of claim 14, wherein hold-up of liquid is determined in accordance with a predetermined scheme represented by the formula:

$$\epsilon_L = 1 - \epsilon_S - \epsilon_G$$

wherein $\epsilon_L$, $\epsilon_S$ and $\epsilon_G$ are values for the hold-up in the reactor of liquid, solid and gas respectively.

16. An apparatus for determining one or more physical characteristics of individual bubbles in a gas-liquid system comprising an in situ probe device adapted for insertion into such gas-liquid system in an area where individual bubbles flow in such system, said probe device comprising a plurality of independent probes, each of said probes having a rounded fibre optic end portion, means for directing a source of incident light onto each of said probes, said rounded end portion having a geometric shape defined by:

(a) for a dome-shaped probe tip $$\sin \alpha = a/R' \quad \text{(i)}$$

$$\sin \beta = b/R' \quad \text{(ii)}$$

wherein α and β are the total reflection angles for gas and liquid respectively, R' is the radius of curvature of the probe, a and b are two characteristic positions in the probe, (b) for a U-shaped probe tip $$\sin \alpha = (R/R+d) \quad \text{(iii)}$$

$$\sin \beta = (R+x/R+d) \quad \text{(iv)}$$

wherein α and β are the total reflection angles for gas and liquid respectively, R is the radius of curvature of the U-shaped probe, d is the fibre optic diameter and x is a characteristic position of the fibre cross-section said probes being spatially arranged relative to each other in a compact fixed manner to permit detection of one or more of such bubble physical characteristics as an individual bubble flows over said probe device, means for detecting a change in light intensity of reflected light emerging from each said probe, means for evaluating said change in light intensities of each said probe over time to determine said one or more bubble physical characteristics, said fibre optic of each probe being sufficiently thin to enable detection of said bubble characteristics for individual bubbles flowing over said probe device.

17. An apparatus of claim 16, wherein each of said fibre optic probe is formed of a material having an index of refraction greater than 1.55 for a particular wavelength of said light source directing means.

18. An apparatus of claim 17, wherein said fibre optic probe is a flint glass.

19. An apparatus of claim 16, wherein said probe device includes a body portion with a plurality of apertures extending therethrough, said apertures extending generally parallel to each other, the number of said apertures being equal to the number of said probes, each of said probes having a protective sheath extending along said probe leaving said rounded tip exposed, said sheath being sealingly fixed in a respective said aperture to position said tip a predetermined distance outwardly of said body portion.

20. An apparatus of claim 16, wherein said probes of each probe device are separated into first and second sets, said first set of probes comprising at least two probes spaced apart a predetermined distance and extending in the direction of flow of said bubbles over said probe device, said second set of probes comprising at least two probes spaced apart a predetermined distance and extending transversely of said direction in which said first set of probes extend.

21. An apparatus of claim 20, wherein said first set of probes comprise two probes spaced apart a predetermined distance less than the average expected cord length of individual bubbles in the system and second set of probes comprise two probes each positioned to a side of an upper probe of said first set, said two probes of said second set being spaced apart a predetermined distance less than the average expected width of individual bubble cap.

22. An apparatus of claim 21, wherein said probes are formed of flint glass optic fibre, said fibre having a diameter of approximately 1 to 3 mm.

23. An apparatus of claim 21, further characterized in first means for measuring a first period of time that an individual bubble takes in flowing over said predetermined and means means calculating bubble velocity based on a value for said first period of time measured by said measuring means, said first means measuring a second period of time that each individual bubble takes in flowing over one of said probes of said first set and means for calculating cord length from the product of said calculated velocity and said measured second period of time, means for comparing relative times when said emerging light intensity significantly changes and means for calculating bubble cap shape from said comparison of relative times based on said predetermined spatial arrangement for said second set of probes.

24. An apparatus of claim 23, wherein a laser produces said source of light.

25. An apparatus of claim 24, wherein said laser is a He/Ne laser emitting light having a wavelength of 0.632 microns.

26. An apparatus of claim 16, wherein each of said probes has a dome-shaped tip.

* * * * *